United States Patent [19]

Tucker et al.

[11] Patent Number: 5,154,841
[45] Date of Patent: * Oct. 13, 1992

[54] PROCESS FOR PREPARING SUBSTITUTED IMIDAZOLINE FABRIC CONDITIONING COMPOUNDS

[75] Inventors: James R. Tucker, Santa Rosa, Calif.; Glen D. Lichtenwalter, Corsicana, Tex.

[73] Assignee: The Procter & Gamble Company, Cincinnati, Ohio

[*] Notice: The portion of the term of this patent subsequent to May 26, 2009 has been disclaimed.

[21] Appl. No.: 707,496

[22] Filed: May 30, 1991

Related U.S. Application Data

[60] Division of Ser. No. 440,841, Dec. 1, 1989, abandoned, which is a continuation-in-part of Ser. No. 287,922, Dec. 22, 1988, abandoned.

[51] Int. Cl.$^5$ .......................................... D06M 10/08
[52] U.S. Cl. .................................. 252/86; 252/8.75; 252/8.8; 252/8.7; 252/8.9; 548/351.1; 548/350.1; 548/352.1
[58] Field of Search .................... 252/8.6, 8.7, 8.75, 252/8.8 R, 8.9; 260/309.6

[56] References Cited

U.S. PATENT DOCUMENTS

| | | | |
|---|---|---|---|
| 3,095,373 | 6/1963 | Blomfield | 252/8.8 |
| 3,408,361 | 10/1968 | Mannheimer | 260/309.6 |
| 3,681,241 | 8/1972 | Rudy | 252/8.75 |
| 3,689,424 | 9/1972 | Berg et al. | 252/110 |
| 3,775,316 | 11/1973 | Berg et al. | 252/8.8 |
| 3,950,285 | 4/1976 | Wolgemuth | 260/18 TN |
| 4,112,235 | 9/1978 | Schmerling | 560/1 |
| 4,127,489 | 11/1978 | Pracht et al. | 252/8.8 |
| 4,153,781 | 5/1979 | Thillier et al. | 528/274 |
| 4,161,604 | 7/1979 | Elster et al. | 548/352 |
| 4,181,676 | 1/1980 | Buysch et al. | 260/463 |
| 4,182,894 | 1/1980 | Miyamura et al. | 548/352 |
| 4,189,593 | 2/1980 | Wechsler et al. | 548/352 |
| 4,212,983 | 7/1980 | Phillips et al. | 548/352 |
| 4,233,451 | 11/1980 | Pracht et al. | 548/354 |
| 4,283,579 | 8/1981 | Yoshida et al. | 568/857 |
| 4,552,704 | 11/1985 | Mark | 260/463 |
| 4,614,613 | 9/1986 | Fikentscher et al. | 548/964 |
| 4,661,267 | 4/1987 | Dekker et al. | 252/8.8 |
| 4,661,269 | 4/1987 | Trinh et al. | 252/8.8 |
| 4,709,045 | 11/1987 | Kubo et al. | 548/352 |
| 4,724,089 | 2/1988 | Konig et al. | 252/8.8 |
| 4,762,645 | 8/1988 | Tucker et al. | 252/544 |
| 4,767,547 | 8/1988 | Straathof et al. | 252/8.8 |
| 4,770,815 | 9/1988 | Baker et al. | 252/8.8 |
| 4,806,255 | 2/1989 | Konig et al. | 252/8.8 |
| 4,933,096 | 6/1990 | Demeyere et al. | 252/8.8 |
| 4,956,447 | 9/1990 | Gossellink et al. | 252/8.8 |
| 5,013,846 | 5/1991 | Walley | 548/352 |

FOREIGN PATENT DOCUMENTS

| | | |
|---|---|---|
| 1102511 | 6/1981 | Canada . |
| 0000406 | 1/1979 | European Pat. Off. . |
| 0001005 | 3/1979 | European Pat. Off. . |
| 0345842 | 12/1989 | European Pat. Off. . |
| 2243806 | 4/1974 | Fed. Rep. of Germany . |
| 8601144 | 2/1986 | Spain . |
| 1515258 | 3/1977 | United Kingdom . |
| 2005269 | 4/1979 | United Kingdom . |
| 1565808 | 4/1980 | United Kingdom . |
| 1601360 | 10/1981 | United Kingdom . |

OTHER PUBLICATIONS

J. March, "Advanced Organic Chemistry: Reactions, Mechanisms, and Structure", pp. 322-323, 1968.
R. Gabriel, "Selective Amidation of Fatty Methyl Esters with N-(2-Aminoethyl)-Ethanolamine Under Base Catalysts", J. of Amer. Oil Chem. Soc., vol. 61, No. 5, 1984.
H. W. Eckert, "Condensation Products from $\beta$-Hydroxyethylenediamine and Fatty Acids or Their Alkyl Esters and Their Application as Textile Softeners in Washing Agents", Fette-Seifen-Anstrichmittel 74:527-533, 1972.
G. D. Markova, Zh. B. Babugoev, K. M. Nametov, "Catalysis of Transesterification by Organotitanium Compounds", Lakokras, Mater. Ikh Primen. (Russian), (2) 8-9, 1988.
G. L. Markova, K. M. Nametov, "Catalysis of Transesterification by Organic Derivatives of Titanium", Polikondensats. Protsessy i Polimery, Nal'Chik (Russian), 88-94, 1986.
R. Puchta, "Cationic Surfactants in Laundry Detergents and Laundry Aftertreatment Aids", J. Am. Oil Chemists' Soc., p. 367, vol. 61, No. 2, pp. 367-376 (Feb. 1984).

*Primary Examiner*—A. Lionel Clingman
*Assistant Examiner*—William S. Parks
*Attorney, Agent, or Firm*—K. L. Stewart; R. A. Dabek; J. J. Yetter

[57] ABSTRACT

Disclosed is a high yield process for preparing di-substituted imidazoline fabric conditioning compounds. In this process, an acylating agent such as fatty acid is reacted with a specific polyamine, and the product of this reaction is thereafter reacted with either a fatty acid ester or glyceride under specifically-defined conditions and in the presence of an esterifying catalyst such as titanium alkoxide. Use of particular reaction conditions and an esterification catalyst significantly increases the yield of di-substituted imidazoline compounds.

4 Claims, No Drawings

PROCESS FOR PREPARING SUBSTITUTED IMIDAZOLINE FABRIC CONDITIONING COMPOUNDS

TECHNICAL FIELD

This is a division of application Ser. No. 07/440,841, filed on Dec. 1, 1989, which is a Continuation-in-part of Ser. No. 07/287,922 filed Dec. 22, 1988, both now abandoned.

The present invention relates to a process for the preparation of a reaction product mixture containing di-substituted imidazoline fabric softening compounds. In particular, it relates to a process which results in a high yield of the desired di-substituted products through the use of a catalyst and minimizes the production of acrylic (open chain) amine/amide by-products and nonesterified imidazolines. Aqueous dispersions containing these di-substituted imidazoline compounds possess desirable storage stability, viscosity, concentratability and fabric conditioning properties and are especially suitable for use in the rinse cycle of a textile laundering operation.

BACKGROUND OF THE INVENTION

Many different types of fabric conditioning agents have been used in rinse-cycle fabric treatment compositions. One class of compounds frequently used as the active component for such compositions includes substantially water-insoluble quaternary nitrogenous compounds having two long alkyl chains. Typical of such materials are ditallow dimethyl ammonium chloride and imidazolinium compounds substituted with two tallow groups.

These materials are normally prepared in the form of a dispersion in water. It is generally not possible to prepare such aqueous dispersions with more than about 10% of cationic softener without encountering severe product viscosity and storage-stability problems. Although more concentrated dispersions of softener materials can be prepared as described in European Patent Application 0,000,406, Goffinet, published Jan. 24, 1979, and United Kingdom Patent Specification 1,601,360, Goffinet, published Oct. 28, 1981, by incorporating certain nonionic adjunct softening materials therein, product viscosity and stability problems become increasingly unmanageable in more concentrated aqueous dispersions and effectively limit the maximum commercial range of applicability to softener active levels in the range from about 15% to about 20%.

The use of substituted imidazoline compounds as fabric conditioning agents is known. Imidazoline salts have been used by themselves or in combination with other agents in the treatment of fabrics. British Patent Specification 1,565,808, Apr. 23, 1980, assigned to Hoechst Aktiengesellschaft, discloses a textile fabric softener composition consisting of an aqueous solution or dispersion of an imidazoline or a salt thereof, or a mixture of such imidazolines or salts thereof. U.S. Pat. No. 4,724,089, Feb. 9, 1988, to Konig, et al., discloses fabric treatment compositions containing di-alkyl imidazoline compounds, or salts thereof, which may have one alkyl chain interrupted by an ester linkage.

The use of imidazolinium salts as fabric conditioning agents is also known. U.S. Pat. No. 2,874,074, Feb. 17, 1969, to Johnson discloses using imidazolinium salts to condition fabrics. U.S. Pat. No. 3,681,241, Aug. 1, 1972, to Rudy, and U.S. Pat. No. 3,033,704, May 8, 1962, to Sherrill, et al., disclose fabric conditioning compositions containing a mixture of imidazolinium salts and other fabric conditioning agents.

Recent patents also disclose processes for making substituted imidazoline compounds. U.S. Pat. No. 4,233,451, Nov. 11, 1980, to Pracht discloses a process to form the imidazoline precursor of an imidazolinium salt by reacting acylating or esterifying agents with alkylene or polyalkylene polyamines. U.S. Pat. No. 4,189,593, Feb. 19, 1980, to Wechsler, et al., discloses a process for making monoalkyl imidazolines involving contacting aminoethylethanolaine with a methyl carboxylate at an elevated temperature, optionally in the presence of a catalyst, and thereafter subjecting the reaction product to two successive heat treatments. The process disclosed in the Wechsler, et al., patent is aimed at maximizing the production of monoalkyl imidazoline and minimizing the esterification of the monoalkyl imidazoline. The product monoalkyl imidazoline is said to be a useful starting material for making amphoteric surfactants. Japanese Laid Open Publication 61-291571 discloses a process for the manufacture of 1,2-di-substituted imidazolines by reacting fatty acids or their esters with dialkylenetriamines.

It has been found that in addition to the imidazoline compounds formed in the above described reactions, acyclic amines/amides are also present. It has also been found that the presence of such acyclic amines in aqueous dispersions containing substituted imidazoline fabric softening compounds can lead to lower phase stability and undesirable viscosity characteristics. Furthermore, rigorous reaction conditions are currently required to form substituted imidazoline fabric softening compounds. Even at high temperatures the esterification is slow and the product yield ranges from 10–35 percent. Therefore, there is a need for a new and improved process for preparing di-substituted imidazolines that minimizes the product of acyclic amines/amides and monoalkyl imidazolines (i.e. nonesterified) and increases the reaction rate and product yield.

It is therefore the object of the present invention to provide a process for making di-substituted imidazoline compounds that minimizes the product of acyclic amine/amide by-products and monoalkyl imidazolines.

It is another object of this invention to provide a high yield process for preparing reaction product mixtures containing these di-substituted imidazoline compounds at a decreased reaction time through the use of a catalyst.

It is another object of this invention to provide fabric conditioning compositions comprising the di-substituted imidazoline compounds prepared using the improved process of this invention.

It is another object of this invention to provide a method for conditioning fabrics by treating them with aqueous dispersions containing the desired di-substituted imidazoline fabric conditioning compounds.

It is still another object of this invention to provide a method for conditioning fabrics by treating them with particular fabric softening and antistatic compositions which have been prepared by the improved process herein and which are in solid form. Such solid compositions are releasably affixed to sheet materials which can be used in hot air clothes dryers.

These and other objects are realized by the present invention.

SUMMARY OF THE INVENTION

The present invention is directed to a process for preparing a reaction product mixture containing di-substituted imidazoline compounds useful as fabric conditioning agents. Such a process comprises:

(a) forming a liquid reaction mixture containing (1) an acylating agent selected from fatty acids of the formula RCOOH, fatty acid halides of the formula RC(O)Y, fatty acid anhydrides of the formula $(RC(O))_2O$, or fatty acid short chain esters of the formula $RC(O)OR^1$, wherein, in these formulas, R is a $C_7-C_{21}$ hydrocarbyl group, $R^1$ is a $C_1-C_4$ alkyl group, and Y is a halide, and (2) a polyamine having the formula $NH_2-(CH_2)_m-NH-(CH_2)_n-X-H$, wherein m and n are, independently, integers from 2-6, and X is O, S, $NR_2$, wherein $R^2$ is H or a $C_1-C_4$ alkyl group, $O(R^3)_p$, $NH(R^3)_p$, or $S(R^3)_p$, wherein $R^3$ is an alkoxy group and p is an integer from 1 to 100, the molar ratio of the acylating agent to the polyamine ranging from about 0.5:1 to 2.0:1;

(b) maintaining this liquid reaction mixture at a temperature of from about 100° C. to 240° C. for a period of time sufficient to convert at least about 50 percent of the polyamine in the mixture to a mono-substituted imidazoline of the formula:

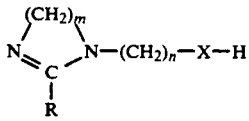

wherein R, m, n and X are as hereinbefore defined; and thereafter (c) adding to the liquid reaction mixture formed in step (b), after drying the liquid reaction mixture if necessary to render it anhydrous, both an esterifying agent and a catalyst, said esterifying agent being selected from $C_1-C_4$ mono-esters of $C_{12}-C_{22}$ fatty acids and $C_{12}-C_{22}$ fatty acid mono-, di-, and tri-glycerides; said esterifying agent being present in an amount sufficient to provide a molar ratio of esterifying agent to acylating agent originally present in step (a) of from about 0.3:1 to 1.5:1; said esterification catalyst being selected from alkali metal alkoxides, transition metal alkoxides, metal halides, transition metal alkyl akoxides, metal alkyl halides, metal carboxylate salts, and tin complexes; and subsequently (d) maintaining this anhydrous liquid reaction mixture at a temperature of from about 1000° C. to 200° C. for a period of time sufficient to form a reaction product mixture which contains a di-substituted imidazoline of the formula:

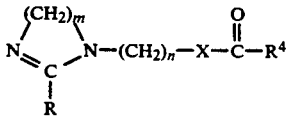

wherein R, m, n, and X are as hereinbefore defined, and wherein $R^4$ is a $C_{11}-C_{21}$ hydrocarbyl.

The present invention also relates to the preparation of aqueous and solid fabric softening compositions using the reaction product mixture formed by the foregoing process and to methods of conditioning fabrics using such compositions.

DETAILED DESCRIPTION OF THE INVENTION

In accordance with this invention, a reaction product mixture containing di-substituted imidazoline compounds is produced. The process disclosed herein results in a higher yield of the desired di-substituted imidazoline compounds, a reduced reaction time necessary for the production of the desired di-substituted imidazoline compounds, and a lower amount of acyclic amine/amide by-products, compared with prior art processes for making substituted imidazoline compounds. A further advantage of the process is that the reaction product mixture which results can be used for preparation of stable, liquid fabric treatment compositions without substantial further processing. The reaction product mixture can also be solidified and used for fabric treatment by releasably affixing it to a solid carrier.

The process to form the reaction product mixture comprising the desired di-substituted imidazoline compounds involves the following steps: (As used herein, all percentages and ratios are by weight unless otherwise specified.)

A. Formation of Mono-Substituted Imidazoline Intermediate

In the first two process steps of the present reaction, a mono-substituted imidazoline precursor (intermediate) for the di-substituted imidazoline product is formed by reacting an acylating agent with a polyalkylene polyamine having 2 or 3, preferably 2 amino groups.

The acylating agent used in these first steps can be selected from fatty acids of the formula $(RC(O))_2O$, or fatty acid short-chain esters of the formula RCOOH, fatty acid halides of the formula RC(O)Y, wherein Y is a halide, preferably Cl or Br, fatty acid anhydrides of the formula $(RC(O)OR^1)$, wherein $R^1$ is a $C_1-C_4$ alkyl group. In all of these formulas R is a $C_7-C_{21}$, preferably $C_{13}-C_{17}$, hydrocarbyl group. As used herein the term "hydrocarbyl group" includes saturated, unsaturated, branched, or straight hydrocarbon chains, each of which may contain one or more functional groups, such as a hydroxyl group, as substituents thereon.

Examples of suitable acylating agents include, but are not limited to, the saturated fatty acids such as stearic (most preferred), lauric, tridecanoic, myristic, pentadecanoic, hexadecanoic, palmitic, behenic and the like; unsaturated fatty acids such as elaidic acid, oleic acid, linolenic acid, and the like; the fatty acid halides such as stearoyl chloride, stearoyl bromide, oleoyl chloride, palmitoyl chloride, myristoyl choride, lauroyl choride, and the like; the fatty acid anhydrides such as stearic anhydride, oleic anhydride, palmitic anhydride, lauric anhydride, linoleic anhydride, behenic anhydride, and the like; and the fatty acid short chain esters such as methyl laurate, methyl myristate, methyl palmitate, methyl stearate, ethyl laurate, ethyl myristate, ethyl palmitate, ethyl stearate, n-propyl laurate, n-propyl myristate, n-propyl palmitate, n-propyl stearate, isopropyl laurate, isopropyl myristate, isoprypyl palmitate, isopropyl stearate, n-butyl laurate, n-butyl myristate, n-butyl palmitate, n-butyl stearate, sec-butyl laurate, sec-butyl myristate, sec-butyl palmitate, sec-butyl stearate, tert-butyl laurate, tert-butyl myristate, tert-butyl palmitate, tert-butyl stearate, and the like.

Examples of branch-chained acylating agents include, but are not limited to, 2-methyl pentadecanoic acid, 2-ethyl pentadecanoic acid, 2-methyl tridecanoic acid, 2-methyl heptadeconic acid, and the like.

Preferred fatty acids, fatty acid halides, fatty acid anhydrides, and fatty acid short chain esters can be derived from tallow, soybean oil, tall oil, coconut oils, and mixtures thereof.

As indicated above, the polyamine material has either 2 or 3, preferably 2, amino groups. In such a polyamide, a primary hydroxyl, amino or sulfhydryl group is preferably int eh β-position to the secondary amino group. Useful polyamines are those of the formula:

where X is O (most preferred), S, $NR^2$, wherein $R^2$ is H or a $C_1-C_4$ alkyl group, $O(R^3)_p$, $NH(R^3)_p$, or $S(R^3)_p$, wherein $R^3$ is an alkoxy group and p is an integer from 1 to 100, and m and n are independently integers from 2 to 6, with n=m=2 being most preferred. Examples of such polyamines include hydroxyethyl ethylenediamine (most preferred) and diethylenetriamine.

In a first step of the process herein, the polyamine and acylating agent as described hereinbefore are combined to form a liquid reaction mixture. In such a mixture, the molar ratio of acylating agent to polyamine will generally range from about 0.5:1 to about 2.0:1, more preferably from about 0.75:1 to about 0.90:1.

Preferably the reaction mixture is rendered in liquid form by heating the reactants above their melting point and by combining the reactants int heir molten state. Optionally, but not preferably, the liquid reaction mixture may also contain solvents known by those skilled in the art to be compatible with the reactants i the liquid reaction mixture. Examples of said solvents include, but are not limited to, water, aliphatic hydrocarbons, aromatic hydrocarbons, (e.g. benzene, xylene, etc.), amines, nitriles, halocarbons (e.g., chlorocarbons), ethers, and glymes. Accordingly, the reaction mixture will generally contain from about 50% to 100% by weight, more preferably from about 75% to 100% by weight, of the reactants. Use of components other than the reactants in the initially formed reaction mixture is not preferred since such non-reactive ingredients may impact reaction conditions as a result of their presence.

The initial reaction mixture, which may or may not be anhydrous, is preferably formed by charging a suitable reaction vessel with liquid (e.g., molten) polyamine and by then adding the molten acylating agent to the vessel while agitating, e.g. stirring, the reaction mixture. The reaction mixture in the vessel will generally be maintained under a vacuum or under an inert atmosphere as hereinafter more fully described.

In a second process step, the liquid reaction mixture as hereinbefore described is maintained under reaction conditions which are sufficient to effect conversion of a substantial amount, i.e. at least about 50%, preferably about 75%, most preferably about 90%, of the polyamine in the reaction mixture to a mono-substituted imidazoline intermediate. Generally such conditions will involve bringing the reaction mixture to a temperature of from about 100° C. to 240° C., preferably from about 150° C. to 210° C., most preferably from about 180° C. to 200° C. The reaction mixture will generally be maintained at this temperature for a period of from about 2 to 24 hours, more preferably from about 4 to 18 hours. An inert gas purge at atmospheric pressure (preferred) or slightly greater may be used. Alteratively the reaction can be run, with or without an inert atmosphere, under a vacuum of from about 0.02 mm Hg to 10 mm Hg, preferably from about 0.2 mm Hg to 2.0 mm Hg. The inert gas purge, and/or vacuum if utilized, may be employed during both the charging of the reactants and throughout the reaction of the polyamine and acylating agent. After maintenance of these reaction conditions, the resulting reaction product mixture will contain primarily the desired intermediate mono-substituted imidazoline plus some of the original acylating material, some of the original polyamine, some of the noncyclized intermediate amine/amide products, and other mixed reaction products.

To illustrate these first steps of the process herein, the reaction of a fatty acid acylating agent with a polyamine to form the mono-substituted imidazoline can be diagrammed as follows:

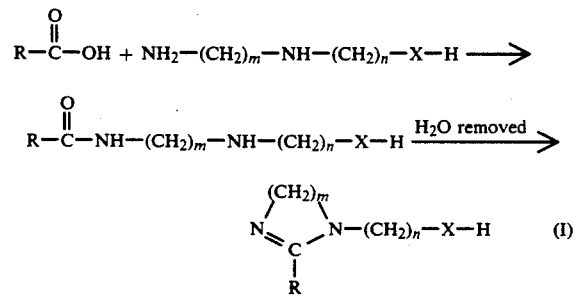

Optionally, the yield of the mono-substituted imidazoline intermediate can be improved by removing water and excess unreacted polyamine during the reaction. This can be effected by stripping with an inert gas purge or vacuum during the entire reaction. The stripped excess polyamine can be recovered and reused. The stripping may be carried out through the use of a distillation apparatus attached to the reaction vessel.

B. Addition of Second Long Chain Alkyl or Substituted Alkyl Group

The mono-substituted imidazoline (I) formed during the first two process steps is further reacted to attach thereto another long chain group of the type desired. In order to achieve this, the mono-substituted imidazoline (I) is further reacted in the same reaction mixture with an added esterifying agent in the presence of a catalytically effective amount of an esterification catalyst.

The esterifying agents useful herein include short chain monoesters of fatty acids and various esters of polyhydric alcohols, such as fatty acid mono-, di- and tri-glycerides. In general the glycerides, and in particular the tri-glycerides, are the most preferred type of esterifying agent.

Tri-glycerides are of course those esters of glycerol which have the general formula:

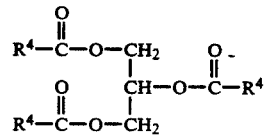

wherein $R^4$ is a $C_{11}-C_{21}$ hydrocarbyl group.

Examples of tri-glycerides include fats and oils derived from tallow, soybean, coconut, cottonseed, sunflower seed, safflower seed, canola, as well as fish oils and tall oils. The hydrogenated (hardened) derivatives of these fats and oils are also suitable.

Examples of suitable di-glycerides include both the 1,3-di-glycerides and the 1,2-di-glycerides, preferably di-glycerides containing two $C_{12}$–$C_{22}$, most preferably two $C_{16}$–$C_{20}$, hydrocarbyl groups, including glycerol-1,2-dilaurate; glycerol-1,3-dilaurate; glycerol-1,2-dimyristate; glycerol-1,3-dimyristate; glycerol-1,2-dipalmitate; glycerol-1,3-dipalmitate; glycerol-1,2-distearate, glycerol-1,3-distearate, 1,2-ditallowalkyl glycerol and 1,3-ditallowalkyl glycerol.

Examples of suitable mono-glycerides include glycerol-1-monolaurate, glycerol-2-monolaurate, glycerol-1-monomyristate, glycerol-2-monomyristate, glycerol-1-monopalmitate, glycerol-2-monopalmitate, glycerol-1-monostearate, and glycerol-2-monostearate.

Another type of esterifying agent useful herein comprises short chain monoesters of fatty acids, which monoesters have the formula:

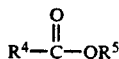

wherein $R^4$ is a $C_{11}$–$C_{21}$ hydrocarbyl group and $R^4$ is a $C_1$–$C_4$ alkyl group.

Example of such fatty acid mono-esters include the $C_1$–$C_4$ esters of lauric, tridecanoic, myristic, pentadecanoic, hexadecanoic, palmitic, oleic, stearic, elaidic, oleic, linolenic, 2-methyl pentadecanoic, 2-ethyl pentadecanoic, 2-methyl heptadecanoic, and 2-methyl tridecanoic fatty acids, with the methyl esters being preferred. Preferred fatty acid methyl esters can be derived from tallow, soybean, coconut or tall oils, and mixtures thereof.

The esterification catalysts useful herein include metal alkoxides, preferably of the formula $Sn(OR^6)_2$ or $Sn(OR^6)_4$, more preferably alkali metal alkoxides of the formula $NaOR^7$ or $KOR^7$, wherein $R^7$ is a $C_1$–$C_6$ alkyl group, most preferably transition metal alkoxides of the formula $Ti(OR^6)_4$, wherein $R^6$ is a $C_1$–$C_4$ alkyl group, preferably $C_2$–$C_3$; metal halides, preferably tin halides or transition metal halides, most preferably of the formula $TiY_4$, wherein Y is a halide, preferably Cl or Br; metal alkyl halides, preferably transition metal alkyl halides; metal carboxylate salts, preferably the acetate or higher carboxylate salts of tin, mercury, lead or zinc, more preferably tin and zinc salts; metal alkyl alkoxides, preferably transition metal alkyl alkoxides; and tin complexes, including, but not limited to, tin alkyls. Preferred tin complexes include $SnT_2$ or $SnT_4$, wherein T is independently a $C_1$–$C_8$ hydrocarbyl group or a hydroxyl group.

Examples of specific esterification catalysts include titanium(IV) tetraethoxide (preferred), titanium(IV) tetraisopropoxide (most preferred), titanium(IV) tetrapropoxide, titanium(IV) tetrachloride, titanium(IV) tetrabromide, titanium(IV) tetramthoxide, sodium methoxide (preferred), sodium ethoxide, sodium isopropoxide, sodium t-butoxide, potassium methoxide, potassium ethoxide, potassium isopropoxide, potassium t-butoxide, zinc acetate (preferred), mercuric acetate, lead acetate, aluminum trichloride, vanadyl trichloride, ethyl aluminum di-chloride, stannous salts such as stannous acetate (preferred), stannous hydroxide, stannous romide, stannous chloride, stannous fluoride, stannous iodide, stannous oxychloride, stannous sulfate, stannous oxide, stannous laurate, stannous octanate, stannous oleate, stannous oxalate, stannous butoxide, stannous 2-ethyl hexoxide, stannous phenoxide, stannous cresoxides, and the like, stannic salts such as stannic chloride, stannic bromide, stannic fluoride, stannic oxychloride, and the like, dialkyltin salts of carboxylic acids such as dibutyltin diacetate, dibutyltin dilaurate, dibutyltin maleate, dilauryltin diacetate, dioctyltin diacetate, and the like, dialkyltin chlorides such as dibutyltin dichloride, dioctyltin dichloride, and the like, dialkyltin oxides (preferred) such as dibutyltin oxide, dioctyltin oxide, dilauryltin oxide, and the like, and trialkyltin hydroxides (preferred) such as trimethyltin hydroxide, tributyltin hydroxide, trioctyltin hydroxide, and the like.

In the third step of the process herein, the esterifying agent and esterification catalyst as described hereinbefore are added in certain amounts to the intermediate-containing reaction mixture resulting from the first two process steps of the process herein. The esterifying agent will be added in amounts such that the molar ratio of esterifying agent to the amount of acylating agent originally added to the reaction mixture in the first process step ranges from about 0.3:1 to 1.5:1, preferably from about 0.75:1 to 1.2:1.

The esterification catalyst is added to the reaction mixture in a catalytically effective amount. Generally the concentration of esterification catalyst will range from about 0.01 to 5.0 weight percent, with the most preferred concentration being about 0.5 weight percent. (Weight percent is expressed on the basis of the total weight of the total reactants.)

As with the reaction mixture formed in the first process step, the reaction mixture formed in this third step after addition of the esterifying agent and catalyst will also be primarily in the liquid state. Thus the esterifying agent will generally be added in liquid, e.g. molten, form. The catalyst will generally be added in the phase in which it exists under standard conditions. The catalyst may have to be finely divided if employed in solid form.

Water may be present in the reaction mixture resulting from the initial reaction between the fatty acid and the polyamine to form the mono-substituted imidazoline intermediate. Any water present must be removed from the reaction mixture before the esterifying agent and esterifying catalyst are added to said reaction mixture. Water generally will be removed continuously form this reaction mixture via an inert gas purge or vacuum employed during the entire duration of the first two process steps. Since water is a product of the reaction between the acylating agent and polyamine, water can affect the reaction equilibrium and its presence can thus prevent the reaction from reaching a maximum yield of mono-substituted intermediate. Substantially all of the water generated during the reaction steps for forming the mono-substituted imidazoline intermediate should be removed. The progress of the reaction can be monitored in order to detect the extent to which water has been stripped from the reaction product mixture resulting from the intermediate-forming steps of the process herein. Methods of monitoring the reaction include, but are not necessarily limited to, weighing the amount of water removed and comparing this with a stoichiometric calculation of the amount of water expected to be generated during the reaction; monitoring the concentration of the initial reactants, the product, or water directly by subjecting samples from the reaction mixture to gas chromatography or high performance liquid chromatography; or monitoring the water content by the Karl Fischer method. It is also necessary that the esterifying agent and esterifying catalyst be anhydrous when added to the reaction product mixture.

No additional solvents or other ingredients need be added to the reaction mixture at this point, although some anhydrous materials could be optionally added. Such materials however, are not necessary for the reaction and may impact the reaction conditions.

After the esterifying agent and esterification catalyst are added, the reaction mixture, in the next process step, is maintained under reaction conditions suitable to effect formation of a reaction product mixture which contains the desired di-substituted imidazoline. In general such conditions will involve brining the reaction mixture to a reaction temperature which ranges from about 100° C. to 200° C., preferably from about 165° C. to 190° C. The mixture will generally be maintained at this temperature for a period of from about 1 to 24 hours, preferably from about 1 to 15 hours, more preferably from about 3 to 5 hours if an alkali metal alkoxide catalyst is utilized, most preferably from about 1 to about 5 hours if a transition metal alkoxide catalyst is utilized. Generally an inert gas purge at atmospheric pressure (preferred) or slightly greater can be used during this step of the process. Alternatively the reaction can be run under a vacuum of from about 0.02 mm Hg to 10 mm Hg, preferably from about 0.2 mm Hg to 2.0 mm Hg. The inert gas purge, or vacuum if utilized, is generally employed during both the charging of the reactants and throughout the reaction of the esterifying agent and the mono-substituted imidazoline intermediate.

To illustrate the last two steps of the process herein, the reaction of the mono-substituted imidazoline (I) formed in the initial reaction steps with a fatty acid ester esterifying agent to form the desired di-substituted imidazoline compounds can be diagrammed as follows:

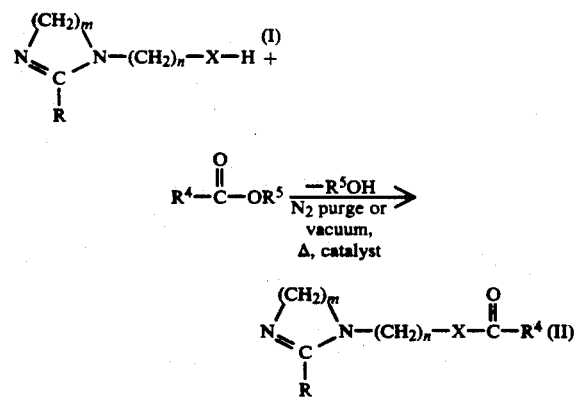

By way of further illustration, the reaction of the mono-substituted imidazoline (I) formed in the initial process steps with a triglyceride esterifying agent to form the desired di-substituted imidazoline compounds can be diagrammed as follows:

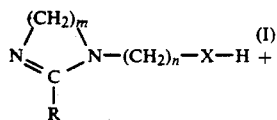

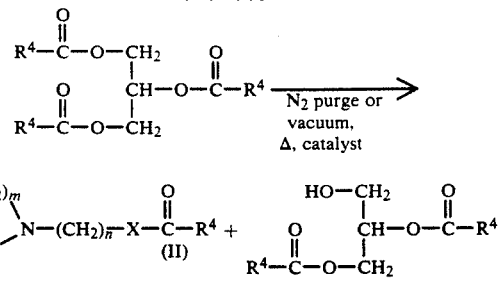

The process herein provides a high yield of the desired di-substituted imidazoline fabric conditioning compounds (II). Such compounds are those di-substituted imidazoline compounds wherein R and $R^4$ in the above formulas are independently $C_{13}$–$C_{17}$ hydrocarbyl groups.

Examples of such di-substituted imidazoline compounds wherein X is O (oxygen) include stearoyl oxyethyl-2-stearyl imidazoline, stearoyl oxyethyl-2-palmotyl imidazoline, stearoyl oxyethyl-2-myristyl imidazoline, palmitoyl oxyethyl-2-palmityl imidazoline, palmitoyl oxyethyl-2-myristyl imidazoline, stearoyl oxyethyl-2-tallow imidazoline, myristoyl oxyethyl-2-tallow imidzoline, palmitoyl oxyethyl-2-tallow imidazoline, coconut esters of oxyethyl-2-coconut imidazoline, tallow esters or oxyethyl-2-tallow imidazoline, and mixtures of such imidazoline compounds.

Examples of such di-substituted imidazoline derivatives wherein X is NH include stearyl amido ethyl-2-stearyl imidazoline, stearyl amido ethyl-2-palmityl imidazoline, stearyl amido ethyl-2-myristyl imidazoline, palmityl amido ethyl-2-palmityl imidazoline, palmityl amido ethyl-2-myristyl imidazoline, stearyl amido ethyl-2-tallow imidazoline, myristyl amido ethyl-2-tallow imidazoline, palmityl amido ethyl-2-tallow imidazoline, coconut amido ethyl-2-coconut imidazoline, tallowamido ethyl-2-tallow imidazoline, and mixtures of such imidazoline compounds.

Examples of such di-substituted imidazoline derivatives wherein X is S (sulfur) include stearylthiolethyl-2-stearyl imidazoline, stearylthiolethyl-2-palmityl imidazoline, stearylthiolethyl-2myristyl imidazoline, palmitylthiolethyl-2-palmityl imidazoline, palmitylthiolethyl-2-myristyl imidazoline, palmitylthiolethyl-2-tallow imidazoline, myristylthiolethyl-2-tallow imidazoline, stearylthiolethyl-2-tallow imidazoline, coconut thiolethyl-2-coconut imidazoline, tallowthiolethyl-2-tallow imidazoline, and mixtures of such compounds.

Without intending to be bound by theory, it is believed that the high yield of the desired di-substituted imidazoline compounds achieved by the process herein primarily results from the use of an esterification catalyst to promote conversion of the mono-substituted imidazoline intermediate to the desired di-substituted imidazoline compounds. Optimal yields are obtained when, as described herein, the synthesis reaction, starting with the polyamine and acylating reactants, is divided into separate steps, with the esterifying agent and esterification catalyst being added after the mono-substituted imidazoline intermediate has been formed. When such a synthesis reaction is carried out in one step by adding polyamine, acylating agent, esterifying agent and catalyst to the reaction mixture initially formed, sub-optimal yields can result.

Other factors which can have a positive effect on the yield obtained include employing relatively high ultimate reaction temperatures, using an inert gas purge, and using ester (especially triglyceride ester) feedstocks as the esterifying agent. Importantly, while the reaction product mixture of the process herein does contain minor amounts of various cyclic imidazolines and acyclic, complex poly-amine/amide by-products, the process of this invention minimizes the production of monoalkyl imidazoline and acyclic amine/amide by-products. This is believed to improve the stability, viscosity, concentratability, and fabric conditioning properties of aqueous fabric softening compositions which are prepared from reaction product mixtures of this type.

Some of the acyclic amine/amide by-products, as well as some of the starting materials, other intermediates, water and other complexes, are present in the reaction product mixture as diluents along with the desired di-substituted imidazoline compounds. These diluents can be detected by methods such as thin layer chromatography, high performance liquid chromatography and gas chromatography. Many of these diluents can be removed during the reaction, if desired, by means of the purging/vacuum procedure. Since the process herein results in a reaction product mixture containing a high yield of the desired di-substituted imidazoline products with minimized production of acyclic amine/amide by-products, the need to later separate out such diluents can be eliminated. That is, the final reaction product mixture provided herein can be used "as is" in the formulation of more dilute, consumer marketable aqueous fabric conditioning compositions.

Fabric Conditioning Compositions

Fabric conditioning compositions containing the substituted imidazoline compounds prepared herein are especially suitable for use in the rinse cycle of a textile laundering operation. Such compositions should contain no more than about 50%, preferably less than about 20%, of uncyclized amine/amide and mono-substituted imidazoline by-products, based on the weight of the desired di-substituted imidazoline compounds. The process of this invention will yield a reaction mixture containing the desired di-substituted imidazoline compounds with relatively low levels of by-products. Use of such reaction mixtures to form fabric conditioning compositions will thus ensure that the compositions made from the reaction product mixtures will not have more than the above-indicated levels of the various undesirable components.

Liquid fabric conditioning compositions of this invention are preferably aqueous and contain from about 1% to about 50% of the reaction product mixture produced by the process of the instant invention [i.e., comprising primarily the di-substituted imidazoline compounds of formula (II)] in a dispersion. Such compositions preferably contain from about 5% to 35%, and most preferably from about 5% to 8%, of the reaction product mixture of the present invention.

Alteratively, solid fabric softening and antistatic compositions can be prepared from the reaction product mixtures produced by the process of this invention. Such solid compositions can be releasably affixed to a solid carrier. As an example, such compositions can be releasably affixed onto a sheet (e.g., paper towel, nonwoven fabric, or the like) and tumbled with damp fabrics in a hot-air clothes dryer, in the manner of the BOUNCE ® brand dryer-added product known in commercial practice. Generally, such solid form compositions will comprise from about 50% to about 100% of the reaction product mixture produced by the process of the instant invention.

Conventional Cationic Nitrogen Containing Fabric Conditioning Agents

In addition to the preferred di-substituted imidazoline compounds, the fabric conditioning compositions of the present invention may also contain other non-imidazoline ester fabric conditioning (softening/antistatic) agents. Such other agents may be described as cationic and nonionic organic materials which are generally employed as fabric conditioning agents during the rinsing cycle of the household laundering process. They are organic, waxy materials having a melting (or softening) point between 25° C. and 115° C. Such materials can possess both fabric softening and fabric antistatic properties.

Generally, said conventional cationic organic materials include nitrogen containing compounds such as quaternary ammonium compounds having one or two straight-chain organic groups of at least eight carbon atoms. Preferably, they have one or two such groups of from 12 to 22 carbon atoms. Preferred cation-active softener compounds include the quaternary ammonium antistat/softener compounds corresponding to the formula:

wherein $A_1$ is hydrogen or an hydrocarbyl group having from 1 to 22 carbon atoms; $A_2$ is an hydrocarbyl group having from 12 to 22 carbon atoms; $A_3$ and $A_4$ are each alkyl groups having from 1 to 3 carbon atoms; and X is an anion selected from halogen, acetate, phosphate, nitrate and methyl sulfate radicals.

Representative examples of quaternary softeners of the invention include ditallow dimethyl ammonium chloride; ditallow dimethyl ammonium methyl sulfate; dihexadecyl dimethyl ammonium chloride; di(hydrogenated tallow) dimethyl ammonium chloride; dioctadecyl diethyl ammonium chloride; dieicosyl dimethyl ammonium chloride; didocosyl dimethyl ammonium chloride; di(hydrogenated tallow) dimethyl ammonium methyl sulfate; dihexadecyl diethyl ammonium chloride; dihexadecyl dimethyl ammonium acetate; ditallow dipropyl ammonium phosphate; ditallow dimethyl ammonium nitrate; di(coconut) dimethyl ammonium chloride, dimethyl di(2-hydroxyethyl) ammonium methylsulfate bis(tallowester), dimethyl di(2-hydroxyethyl) ammonium chloride bis(stearylester), dimethyl di(2-hydroxypropyl) ammonium methylsulfate bis(hard tallowester), diethyl di(2-hydroxyethyl) ammonium ethyl sulfate bis(coconut ester), diethyl di(2-hydroxyethyl) ammonium chloride bis (hexadecanoic ester), and the like.

Another preferred class of fabric conditioning compounds are mono-ester analogs of the quaternary ammonium antistat/softener of formula (III), wherein X is as hereinbefore defined; $A_1$ and $A_2$ are, independently, short-chain ($C_1$–$C_6$, preferably $C_1$–$C_3$) alkyl or hydroxyalkyl substituents; $A_4$ is a long-chain hydrocarbyl substituent in the $C_{16}$-$C_{18}$ range, preferably $C_{18}$ alkyl, most preferably straight-chain alkyl; and $A_3$ is a long-chain esterified hydrocarbyl substituent of the formula:

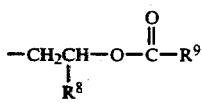

wherein $R^8$ is hydrogen (preferred), a hydroxyl, group or a short-chain ($C_1$-$C_4$) hydrocarbyl substituent, especially methyl, and $R^9$ is a long-chain hydrocarbyl substituent in the $C_{13}$-$C_{15}$ range, preferably $C_{15}$ alkyl, especially straight-chain alkyl.

As illustrative, nonlimiting examples there can be mentioned the following:

$[CH_3]_2[C_{18}H_{37}]^+NCH_2CH(CH_3)OC(O)C_{15}H_{31}Br^{13}$
$[C_2H_5]_2[C_{17}H_{35}]^+NCH_2CH_2OC(O)C_{13}H_{27}Cl^-$
$[C_2H_5][CH_3][C_{18}H_{37}]^+NCH_2CH_2OC(O)C_{14}H_{29}CH_3SO_4^-$
$[C_3H_7][C_2H_5][C_{16}H_{33}]^+NCH_2CH_2OC(O)C_{15}H_{31}Cl^-$
$[iso\text{-}C_3H_7][CH_3[]C_{18}H_{37}]^+NCH_2CH_2OC(O)C_{15}H_{31}I^-$
$[CH_3]_2[C_{18}H_{37}]^+NCH_2CH(OH)CH_2OC\text{-}(O)C_{15}H_{31}Cl^-$
$[C_2H_5]_2[C_{17}H_{35}]^+NCH_2CH(OH)CH_2OC\text{-}(O)C_{14}H_{29}CH_3SO_4^-$ Examples of other conventional quaternary ammonium salts include methylbis (tallowamidoethyl) (2-hydroxyethyl) ammonium methylsulfate, methylbis (hydrogenated tallowamidoethyl) (2-hydroxyethyl) ammonium methylsulfate, 1-methyl-1-tallowamidoethyl-2-tallowimidazolinium methylsulfate and 1-methyl-1-(hydrogenated tallowamidoethyl) methylsulfate. These materials are available from Sherex Chemical Company under the trade names Varisoft ® 222, Varisoft ® 110, Varisoft ® 475, and Varisoft ® 445, respectively.

Nonionic fabric antistat/softener materials include a wide variety of materials, including sorbitan esters, fatty alcohols and their derivatives, imidazolines, and the like. One preferred type of nonionic fabric antistat/softener material comprises the esterified cyclic dehydration products of sorbitol, i.e., sorbitan esters such as sorbitan ester fabric antistat/softener materials herein comprise sorbitan monolaurate, sorbitan monomyristate, sorbitan monopalmitate, sorbitan monolstearate, sorbitan monobehenate, sorbitan dilaurate, sorbitan dimyristate, sorbitan dipalmitate, sorbitan distearate, sorbitan dibehenate, and mixtures thereof, and the mixed coconutalkyl sorbitan mono- and di-esters and the mixed tallowalkyl sorbitan mono- and di-esters. The tri- and tetra-esters of sorbitan with lauric, myristic, palmitic, stearic and behenic acids, and mixtures thereof, are also useful herein.

Examples of imidazoline compounds useful herein include stearyl amido ethyl-2-stearyl imidazoline, stearyl amido ethyl-2-palmityl imidazoline, stearyl amideo ethyl-2-myristyl imidazoline, palmityl amido ethyl-2-palmityl imidazoline, palmityl amido ethyl-2-myristyl imidazoline, stearyl amido ethyl-2-tallow imidazoline, myristyl amido ethyl-2-tallow imidazoline, palmityl amido ethyl-2-tallow imidazoline, coconut amido ethyl-2-coconut imidazoline, tallow amido ethyl-2-tallow imidazoline, hard tallow amido ethyl-2-tallow imidazoline, and the like.

Another useful type of nonionic fabric antistat/softener material encompasses the substantially water-insoluble compounds chemically classified as fatty alcohols. Mono-ols, di-ols, and poly-ols having the requisite melting points and water-insolubility properties set forth above are useful herein. Such alcohol-type fabric conditioning materials also include the mono- and di-fatty glycerides which contain at least one "free" OH group.

All manner of water-insoluble, high melting alcohols (including mono- and di-glycerides) are useful herein, inasmuch as all such materials are fabric substantive.

A preferred type of unesterified alcohol includes the higher melting numbers of the so-called fatty alcohol class. Mono- and di-ether alcohols, especially the $C_{10}$-$C_{18}$ di-ether alcohols having at least one free -OH group, also fall within the definition of alcohols useful as fabric antistat/softener materials herein. The ether-alcohols can be prepared by the classic Williamson ether synthesis.

Ether-alcohols useful herein include glycerol-1,2-dilauryl ether; glycerol-1,3-distearyl ether; and butane tetra-ol-1,2,3-trioctanyl ether.

Other Optional Ingredients

Other adjuvants can also be added to the fabric softening compositions herein for their known purposes. Such adjuvants include, but are not limited to, viscosity control agents, perfumes, emulsifiers, preservatives, antioxidants, bactericides, fungicides, colorants, dyes, brighteners, opacifiers, freeze-thaw control agents, shrinkage control agents, and agents to provide ease of ironing. These adjuvants, if used, are added at their usual levels.

Viscosity control agents can be organic or inorganic in nature. Examples of organic viscosity modifiers are fatty acids and esters, fatty alcohols, and water-miscible solvents such as short chain alcohols. Examples of inorganic viscosity control agents are water-soluble ionizable salts. A wide variety of ionizable salts can be used. Examples of suitable salts are the halides of the group IA and IIA metals of the Periodic Table of the Elements, e.g., calcium chloride, magnesium chloride, sodium chloride, potassium bromide, and lithium chloride. Calcium chloride is preferred. The ionizable salts are particularly useful during the process of mixing the ingredients to make the compositions herein, and later to obtain the desired viscosity. The amount of ionizable salts used depends on the amount of active ingredients used in the compositions and can be adjusted according to the desires of the formulator. Typical levels of salts used to control the composition viscosity are from about 20 to about 6,000 parts per million (ppm), preferably from about 20 to about 4,000 ppm, by weight of the composition.

Examples of bactericides used in the compositions of this invention are glutaraldehyde, formaldehyde, 2-bromo-2-nitropropane-1,3-diol sold by Inolex Chemicals under the tradename Bronopol ®, and a mixture of 5-chloro-2-methyl-4-isothiazoline-3-one and 2-methyl-4-isothiazoline-3-one sold by Rohm and Haas Company under the trade name Kathon ® CG/ICP. Typical levels of bactericides used in the present compositions are from about 1 to about 1,000 ppm by weight of the composition.

Examples of antioxidants that can be added to the compositions of this invention are propyl gallate, available from Eastman Chemical Products, Inc., under the trade names Tenox ® PG and Tenox ® S-1, and butylated hydroxy toluene, available from UOP Process Division under the trade name Sustane ® BHT.

The fabric softening compositions of this invention may also contain silicones to provide additional benefits such as improved fabric feel. The preferred silicones are polydimethylsiloxanes of a viscosity of from about 100 centistokes (cs) to about 100,000 cs, preferably from about 200 cs to about 60,000 cs. These silicones can be used as is, or can be conveniently added to the softener compositions in a preemulsified form which is obtainable directly from the suppliers. Examples of these preemulsified silicones are 60% emulsion of polydimethylsiloxane (350 cs) sold by Dow Corning Corporation under the trade name Dow Corning ® 1157 Fluid, and 50% emulsion of polydimethylsiloxane (10,000 cs) sold by General Electric Company under the trade name General Electric ® SM 2140 Silicones. The optional silicone component can be used in an amount of from about 0.1% to about 6% by weight of the composition.

Other minor components include short chain alcohols such as ethanol and isopropanol which are present in the commercially available quaternary ammonium compounds that may be used in the preparation of the present compositions. The short chain alcohols are normally present at from about 1% to about 10% by weight of the composition.

A preferred composition contains from about 0.2% to about 2% of perfume, from 0% to about 3% of polydimethyl-siloxane, from 0% to about 0.4% of calcium chloride, from about 1 ppm to about 1,000 ppm of bactericide, from about 10 ppm to about 100 ppm of dye, and from 0% to about 10% of short chain alcohols, by weight of the total composition.

It is expected that limiting the pH of the fabric softening compositions of this invention to the range of from about 2 to about 8, preferably from about 2.5 to about 5, will beneficially enhance the stability of the composition. Adjustment of pH is normally carried out by including a small quantity of free acid in the formulation. Because no strong pH buffers are present, only small amounts of acid are required. Any acidic material can be used; its selection can be made by anyone skilled in the softener arts on the basis of cost, availability, safety, etc. Among the acids that can be used are hydrochloric, sulfuric, phosphoric, citric, maleic, and succinic. For the purposes of this invention, pH is measured by a glass electrode in a full strength softening composition.

It is also expected that controlling the particle size diameter of the softener active(s) of the fabric softening compositions of this invention to less than 1 micron, preferably in the range of 0.10-0.50 micron, will beneficially enhance the stability of the composition.

Processing

The aqueous fabric conditioning compositions herein can be prepared by adding the reaction product mixtures of the present invention [i.e., those containing di-substituted imidazoline fabric softening compounds (II)] to water using conventional techniques. A convenient and satisfactory method is to first mix the reaction product mixture containing the di-substituted imidazoline compounds, as prepared by the process herein, with isopropanol. This combination is maintained at, or if necessary reheated to, a temperature of from about 60° C. to about 90° C. to form a fluidized "melt". The melt is poured into an acidified water seat (heated from about 50° C. to about 75° C.) and mixed with high shear agitation to form an aqueous dispersion. The composition can then be adjusted to a pH of from about 2 to about 8, preferably from about 2.5 to 5. Optional ingredients can be added according to methods known in the art.

A method for preparing solid fabric softening compositions releasably affixed to a carrier substrate is to first mix the reaction product mixture, as prepared herein, with isopropanol. Optional ingredients can be added according to methods known in the art. This combination is then heated to a temperature of from about 60° C. to about 90° C. to form a fluidized "melt". The carrier substrate is then coated with about 4 grams of the fluidized melt and dried overnight. Following solidification of the fabric conditioning composition, the substrate is slit with a knife, said slits being substantially parallel and extending to within 1 inch from at least one edge of the substrate. The width of an individual slit is approximately 0.2 inches.

Composition Usage

In the method aspect of this invention, fabrics or fibers are contacted with an effective amount, generally from about 20 ml to about 200 ml (per 3.5 kg of fiber or fabric being treated), of the fabric compositions herein added to an aqueous bath. Of course, the amount used is based upon the judgment of the user, depending on concentration of the composition, fiber or fabric type, degree of softness desired, and the like. Typically, from about 65 ml to 120 ml, preferably about 68 ml, of a dispersion containing from about 4% to 50%, preferably 8%, of the di-substituted imidazoline softening compound, optionally containing additional softening compounds, is used in a 25 l laundry rinse bath to soften and provide antistatic benefits to a 3.5 kg load of mixed fabrics. Such concentration levels achieve superior fabric softening and static control.

In general, the invention herein in its fabric conditioning method aspect comprises: (a) washing fabrics in a conventional automatic washing machine with a detergent composition (normally containing a detersive surfactant or mixture of surfactants selected from the group consisting of anionic, nonionic, amphoteric or ampholytic surfactants); (b) rinsing the fabrics; and (c) adding during the final rinse stage of the operation the above-described levels of the fabric conditioning composition. An alternative to step (c) is adding solid fabric softening compositions releasably affixed to a carrier substrate to a clothes dryer together with damp fabrics to be treated.

The fabrics may be dried either in a mechanical dryer at a temperature of at least about 38° C., which may be utilized whether the softening composition is in an aqueous dispersion or a solid form, or by suspending the fabrics from a clothes line, which may be utilized only when the softening compositions is in an aqueous dispersion. The mechanical dryer is preferred, as it facilitates spreading of the fabric conditioning materials herein across the fabric surfaces.

EXAMPLES

The following exemplify the various synthesis, compositional and method of use aspects of the present invention. These examples are merely illustrative of the invention and should not be considered as limiting.

EXAMPLE I

A reaction product mixture containing a di-substituted imidazoline ester fabric conditioning compound is prepared in the following manner:

A three-necked, two-liter flask, equipped with a reflux condenser, nitrogen inlet and overhead stirrer, is charged with 1.0 mole of stearic acid, sparged with $N_2$ and heated to 70° C. (melted). With stirring, 1.1 mole of polyamine of the formula $NH_2(CH_2)_2NH(CH_2)_2OH$ is added. The reaction mixture is heated and stirred at 160° C. for 3 hours. The reflux condenser is then removed, and the $N_2$ sparge is increased as the reaction mixture is heated to 200° C. for and additional 4 hours, during which time water and excess amine are swept out in the $N_2$ stream. At this point approximately 90% of the polyamine will have been converted to a mono-substituted imidazoline. The reaction mixture is cooled to room temperature overnight under a $N_2$ flow. The dry reaction mixture is then heated to melting (70° C.) and 1.0 mole of dry methyl stearate is added along with 0.005 mole $Ti(OCH(CH_3)_2)_4$. The reaction mixture is heated to 180° C. and held at that temperature for approximately 2.5 hours. The resulting reaction product mixture comprises approximately 87% by weight of stearoyl-oxyethyl-2-heptadecyl imidazoline, and contains a minimum amount of mono-substituted imidazoline and acyclic amine/amide by-products.

EXAMPLE II

A reaction product mixture containing a di-substituted imidazoline ester fabric conditioning compound is prepared in the following manner:

A three-necked, two-liter flask, equipped with a reflux condenser, nitrogen inlet and overhead stirrer, is charged with 1.0 mole of stearic acid, sparged with $N_2$ and heated to 70° C. (melted). With stirring, 1.1 mole of polyamine of the formula $NH_2(CH_2)_2NH(CH_2)_2OH$ is added. The reaction mixture is heated and stirred at 160° C. for 3 hours. The reflux condenser is then removed, and the $N_2$ sparge is increased as the reaction mixture is heated to 200° C. for an additional 4 hours, during which time water and excess amine are swept out in the $N_2$ stream. At this point approximately 90% of the polyamine will have been converted to a mono-substituted imidazoline. The reaction mixture is cooled to room temperature overnight under a $N_2$ flow. The dry reaction mixture is then heated to melting (70° C.) and 0.34 mole dry tristearyl-glycerine is added along with 0.005 mole $Sn(CH_3CO_2)_2$. The reaction mixture is then heated to 180° C. and held at that temperature for approximately 2.5 hours. The resulting reaction product mixture comprises approximately 82% by weight of stearoly-oxyethyl-2-stearyl imidazoline, and contains a minimum amount of mono-substituted imidazoline and acyclic amine/amide by-products.

EXAMPLE III

A reaction product mixture containing a di-substituted imidazoline ester fabric conditioning compound is prepared in the following manner:

a three-necked, two-liter flask, equipped with a reflux condenser, nitrogen inlet and overhead stirrer, is charged with 1.5 mole of palmitic acid, sparged with $N_2$ and heated to 70° C. (melted). With stirring, 2.0 mole of polyamine of the formula $NH_2(CH_2)_2NH(CH_2)_2OH$ is added. The reaction mixture is heated and stirred at 160° C. for 3 hours. The reflux condenser is then removed, and the $N_2$ sparge is increased as the reaction mixture is heated to 200° C. for an additional 4 hours, during which time water and excess amine are swept out in the $N_2$ stream. At this point approximately 90% of the polyamine will have been converted to a mono-substituted imidazoline. The reaction mixture is cooled to room temperature overnight under a $N_2$ flow. The dry reaction mixture is then heated to melting (70° C.) and 1.5 mole dry methyl palmitate is added along with 0.01 mole $CH_3CH_2AlCl_2$. The reaction mixture is heated to 180° C. and held at that temperature for approximately 2.5 hours, or the length of time necessary to complete the reaction (monitored by TLC, infrared, GC or acid and amine values). The resulting reaction product mixture comprises at least 75% by weight of palmitoyloxy-ethyl-2-pentadecyl imidazoline, and contains a minimum amount of mono-substituted imidazoline and acyclic amine/amide by-products.

EXAMPLE IV

A reaction product mixture containing a di-substituted imidazoline ester fabric conditioning compound is prepared in the following manner:

A three-necked, two-liter flask, equipped with a reflux condenser, nitrogen inlet and overhead stirrer, is charged with 1.5 mole of myristic acid, sparged with $N_2$ and heated to 70° C. (melted). With stirring, 2.0 mole of polyamine of the formula $NH_2(CH_2)_2NH(CH_2)_2OH$ is added. The reaction mixture is then and stirred at 160° C. for 3 hours. The reflux condenser is then removed, and the $N_2$ sparge is increased as the reaction mixture is heated to 200° C. for an additional 4 hours, during which time water and excess amine are swept out in the $N_2$ stream. At this point approximately 90% of the polyamine will have been converted to a mono-substituted imidazoline. The reaction mixture is cooled to room temperature overnight under a $N_2$ flow. The dry reaction mixture is then heated to melting (70° C.) and 1.5 mole dry methyl myristate is added along with 0.10 mole $NaOCH_3$. The reaction mixture is heated to 180° C. and held at that temperature for approximately 2.5 hours, or the length of time necessary to complete the reaction. The resulting reaction product mixture comprises at least 75% by weight of myristoyloxyethyl-2-tridecyl imidazoline, and contains a minimum amount of mono-substituted imidazoline and acyclic amine/amide by-products.

EXAMPLE V

A reaction product mixture containing a di-substituted imidazoline amide fabric conditioning compound is prepared in the following manner:

A three-necked, two-liter flask, equipped with a reflux condenser, nitrogen inlet and overhead stirrer, is charged with 1.5 mole of stearic acid, sparged with $N_2$ and heated to 70° C. (melted). With stirring, 2.0 mole of polyamine of the formula $NH_2(CH_2)_2NH (CH_2)_2NH_2$ is added. The reaction mixture is heated and stirred at 160° C. for 3 hours. The reflux condenser is then removed, and the $N_2$ sparge is increased as the reaction mixture is heated to 200° C. for an additional 4 hours, during which time water and excess amine are swept out in the $N_2$ stream. At this point approximately 90% of the polyamine will have been converted to a mono-substituted imidazoline. The reaction mixture is cooled to room temperature overnight under a $N_2$ flow. The dry reaction mixture is then heated to melting (70° C.) and 1.5 mole of dry methyl stearate is added along with 0.01 mole $[CH_3(CH_2)_3]_2Sn(O)$. The reaction mixture is heated to 180° C. and held at that temperature for approximately 2.5 hours, or the length of time necessary to complete the reaction. The resulting reaction product mixture comprises at least 75% by weight of 1-stearoylamido-ethyl-2-heptadecyl imidazoline, and contains a minimum amount of mono-substituted imidazoline and acyclic amine/amide by-products.

EXAMPLE VI

A reaction product mixture containing a di-substituted imidazoline thiolester fabric conditioning compound is prepared in the following manner:

A three-necked, two-liter flask, equipped with a reflux condenser, nitrogen inlet and overhead stirrer, is charged with 1.5 moles of stearic acid, sparged with $N_2$ and heated to 70° C. (melted). With stirring, 2.0 moles of aminoethylamino thiol is added. The reaction mixture is heated and stirred at 160° C. for 3 hours. The reflux condenser is then removed, and the $N_2$ sparge is increased as the reaction mixture is heated to 200° C. for an additional 4 hours, during which time water and excess amine are swept out in the $N_2$ stream. At this point approximately 90% of the polyamine will have been converted to a mono-substituted imidazoline. The reaction mixture is cooled to room temperature overnight under a $N_2$ flow. The dry reaction mixture is then heated to melting (70° C.) and 1.5 moles dry methyl stearate is added along with 0.02 mole $Sn(CH_3CO_2)_2$. The reaction mixture is then heated to 180° C. and held at that temperature for approximately 2.5 hours. The resulting reaction product mixture comprises at least 75% by weight of stearylthiolethyl-2-stearyl imidazoline, and contains a minimum amount of mono-substituted imidazoline and acyclic amine/amide by-products.

Additional changes in processing conditions, such as using high surface area reactors and reducing pressure to remove condensation by-products, will increase yield, purity and reduce reaction time in Examples I-VI.

EXAMPLE VII

The preparation of a liquid fabric softening composition for use in the rinse cycle of a standard laundering operation as follows:

| Ingredient | Percent (wt.) |
| --- | --- |
| Stearoyloxyethyl-2-heptadecyl imidazoline[1] | 4.5 |
| Isopropanol | 0.6 |
| 0.1 N HCl | 0.25 |
| Water + minors[2] | Balance |

[1]found in the reaction product mixture of Example I.
[2]minors include viscosity control agents, perfumes, emulsifiers, preservatives, antioxidants, bactericides, fungicides, colorants, dyes, brighteners, opacifiers, freeze-thaw control agents, shrinkage control agents, and agents to provide ease of ironing.

The preparation of the liquid fabric softening composition of Example VII is carried out as follows: 18 g of the di-substituted imidazoline reaction product mixture and 2.4 g of isopropanol are mixed and heated to 75° C. to form a fluidized "melt". The melt is then poured into a 375 g acidified water seat with high shear mixing. The water is preheated to 70° C. The dispersion is mixed for 15 minutes at 7000 rpm (Tekmar ® high shear mixer). The pH is adjusted to 4 by the addition of 1 ml of 0.1N HCl. The resulting composition has a viscosity of 40 centipoise (at 25° C.) and is used in standard fashion as a rinse-added fabric softener.

When multiple rinses are used in a fabric laundering operation, the fabric softening composition as prepared here is preferably added to the final rinse. The amount added to the rinse cycle is generally from about 20 ml to about 2000 ml (per 3.5 kg of fabric being treated).

EXAMPLE VIII

The preparation of a liquid fabric softening composition for use in the rinse cycle of a standard laundering operation is follows:

| Ingredient | Percent (wt.) |
| --- | --- |
| Tallowoxyethyl-2-tallow imidazoline | 23.2 |
| 0.1 N HCl | 1.37 |
| $CaCl_2$ | 0.2 |
| Water + minors[1] | Balance |

[1]minors include those ingredients listed as minors in Example VII.

The preparation of the fabric softening composition of Example VIII is carried out in substantially the same manner as the preparation of the fabric softening composition of Example VII.

EXAMPLE IX

The preparation of a liquid fabric softening composition for use in the rinse cycle of a standard laundering operation is as follows:

| Ingredient | Percent (wt.) |
| --- | --- |
| Tallowoxyethyl-2-tallow imidazoline | 15.8 |
| Ditallow dimethyl ammonium chloride | 4.93 |
| 0.1 N HCl | 0.93 |
| Isopropanol | 0.87 |
| Water + minors[1] | Balance |

[1]minors include those ingredients listed as minors in Example VII.

The preparation of the fabric softening composition of Example IX is carried out in substantially the same manner as the preparation of the fabric softening composition of Example VII.

EXAMPLE X

The preparation of a liquid fabric softening composition for use in the rinse cycle of a standard laundering operation is as follows:

| Ingredient | Percent (wt.) |
| --- | --- |
| Tallowoxyethyl-2-tallow imidazoline | 15.8 |
| $[CH_3]_2[C_{18}H_{37}]^+NCH_2CH(CH_3)OC(O)C_{15}H_{31}$ | 4.93 |
| 0.1 N HCl | 0.93 |
| Isopropanol | 0.87 |
| Water + minors[1] | Balance |

[1]minors include those ingredients listed as minors in Example VII.

The preparation of the fabric softening composition of Example X is carried out in substantially the same manner as the preparation of the fabric softening composition of Example VII.

Substantially similar results are obtained if the imidazoline ester softener active in Examples VII-X are replaced, in whole or in part, with the reaction products prepared in Examples II, III, IV, V and VI respectively.

EXAMPLE XI

A dryer-additive sheet is prepared by warming 3 grams of reaction product mixture from any of the above Examples in 6 grams of isopropyl alcohol to prepare a melt in the manner of Example VII. The melt is evenly spread onto and into an ordinary, disposable non-woven rayon sheet (20 mm × 20 cm) and allowed to dry. In use, the impregnated sheet is commingled and tumbled with wet fabrics (5 kg load of fabrics, dry weight basis) in a standard hot air clothes dryer until the fabrics are dry, to provide a soft, antistatic finish.

What is claimed is:

1. An aqueous fabric softening composition comprising from about 1% to about 50% of the reaction mixture produced in a process wherein said reaction product mixture contains di-substituted imidazoline compounds useful as fabric conditioning agents, said process comprising:

a) forming a liquid reaction mixture containing (1) an acylating agent selected from fatty acids of the formula RCOOH, fatty acid halides of the formula RC(O)Y, fatty acid anhydrides of the formula $(RC(O))_2O$, or fatty acid short chain esters of the formula $RC(O)OR^1$, wherein, in said formulas, R is a $C_7-C_{21}$ hydrocarbyl group, $R^1$ is a $C_1-C_4$ alkyl group, and Y is a halide, and (2) a polyamine having the formula $NH_2-(CH_2)_m-NH-(CH_2)_n-X-H$, wherein m and n are, independently, integers from 2-6, and X is O, S, $O(R^3)p$, or $S(R^3)p$, wherein $R^3$ is an alkoxy group and p is an integer from 1 to 100, the molar ratio of the acylating agent to the polyamine ranging from about 0.75:1 to 0.90:1;

b) maintaining said liquid reaction mixture at a temperature of from about 100° C. to 240° C. for a period of time sufficient to convert at least about 50 percent of the polyamine in the mixture to a mono-substituted imidazoline of the formula:

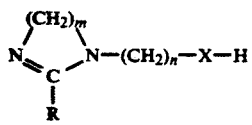

wherein R, m, n and X are as hereinbefore defined; the improvement comprising:

c) adding to said liquid reaction mixture formed in step (b), after drying if necessary to form an anhydrous mixture, both an esterifying agent and a catalytically effective amount of an esterification catalyst, said esterifying agent being selected from $C_1-C_4$ mono-esters of $C_{12}-C_{22}$ fatty acids and $C_{12}-C_{22}$ fatty acid mono-, di-, and tri-glycerides; said esterifying agent being present in an amount sufficient to provide a molar ratio of esterifying agent to acylating agent originally present in step (a) of from about 0.75:1 to 1.2:1;

said esterification catalyst being selected from transition metal alkoxides of the formula $Ti(OR^6)_4$, wherein $R^6$ is a $C_1-C_4$ alkyl group, transition metal alkyl alkoxides, transition metal halides, transition metal alkyl halides, stannous salts, dialkyltin chlorides and $SnT_2$, wherein T is, independently, a $C_1-C_8$ hydrocarbyl group, a hydroxyl group, or a halide; and subsequently;

d) maintaining said anhydrous liquid reaction mixture at a temperature of from about 100° C. to 200° C. for a period of time ranging from about 1 to 5 hours to form a reaction product mixture which contains one or more di-substituted imidazolines of the formula:

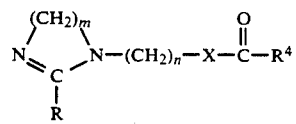

wherein R, m, n and X are as hereinbefore defined, and wherein $R^4$ is a $C_{11}-C_{21}$ hydrocarbyl.

2. An aqueous fabric softening composition comprising from about 1% to about 50% of the reaction mixture produced in a process wherein said reaction product mixture contains di-substituted imidazoline compounds useful as fabric conditioning agents, said process comprising:

a) forming a liquid reaction mixture containing (1) an acylating agent selected from fatty acids of the formula RCOOH, fatty acid halides of the formula RC(O)Y, fatty acid anhydrides of the formula $(RC(O))_2O$, or fatty acid short chain esters, of the formula $RC(O)OR^1$, wherein, in said formulas, R is a $C_7-C_{21}$ hydrocarbyl group, $R^1$ is a $C_1-C_4$ alkyl group, and Y is a halide, and (2) a polyamine having the formula "$NH_2-(CH_2)_m-NH-(CH_2)_n 13 X-H$", wherein m and n are, independently, integers from 2-6, and X is O, S, $O(R^3)_p$, or $S(R^3)_p$, wherein $R^3$ is an alkoxy group and p is an integer from 1 to 100, the molar ratio of the acylating agent to the polyamine ranging from about 0.75:1 to 0.90:1;

b) maintaining said liquid reaction mixture at a temperature of from about 100° C. to 240° C. for a period from about 4 hours to about 18 hours at atmospheric pressure under an inert gas, converting at least 90 percent of the polyamine in the mixture to a mono-substituted imidazoline of the formula:

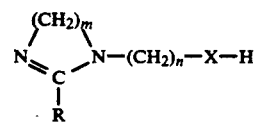

wherein R, m, n and X are as hereinbefore defined; the improvement comprising:

c) adding to said liquid reaction mixture formed in step (b), after drying if necessary to form an anhydrous mixture, both an esterifying agent and a catalytically effective amount of an esterification catalyst, said esterifying agent being of the formula:

wherein $R^4$ is a $C_{11}-C_{21}$ hydrocarbyl group and $R^5$ is a $C_1-C_4$ alkyl group;

said esterifying agent being present in an amount sufficient to provide a molar ratio of esterifying agent to acylating agent originally present in step (a) of from about 0.75:1 to 1.2:1;

said esterification catalyst being selected from $Ti(OR^6)_4$, wherein $R^6$ is a $C_1-C_4$ alkyl group, $TiY_4$, wherein Y is a halide; wherein T is, independently, a $C_1-C_8$ hydrocarbyl group, a hydroxyl group, or a halide and a dialkyltin chloride; and a dialkyltin chloride; and subsequently d) maintaining said anhydrous liquid reaction mixture at a temperature of from about 100° C. to 200° C. for a period of from about 1 to about 5 hours under an inert gas, producing a reaction product mixture containing one or more di-substituted imidazolines of the formula:

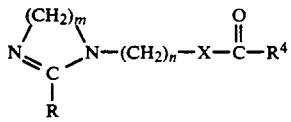

wherein R, R$^4$, m, n and X are as hereinbefore defined.

3. An aqueous fabric softening composition comprising from about 1% to about 50% of the reaction mixture produced in a process wherein said reaction product mixture contains di-substituted imidazoline compounds useful as fabric conditioning agents, said process comprising:

a) forming a liquid reaction mixture containing (1) an acylating agent selected from fatty acids of the formula RCOOH, fatty acid halides of the formula RC(O)Y, fatty acid anhydrides of the formula (RC(O))$_2$O, or fatty acid short chain esters of the formula RC(O)OR$^1$, wherein, in said formulas, R is a C$_7$-C$_{21}$ hydrocarbyl group, R$^1$ is a C$_1$-C$_4$ alkyl group, and Y is a halide, and (2) a polyamine having the formula NH$_2$—(CH$_2$)$_m$—NH—(CH$_2$)$_n$—X—H, wherein m and n are, independently, integers from 2–6, and X is O, S, O(R$^3$)p, or S(R$^3$)p, wherein R$^3$ is an alkoxy group and p is an integer from 1 to 100, the molar ratio of the acylating agent to the polyamine ranging from about 0.75:1 to 0.90:1;

b) maintaining said liquid reaction mixture at a temperature of from about 100° C. to 240° C. for a period of from about 4 hours to about 18 hours at atmospheric pressure under an inert gas, converting at least 90 percent of the polyamine in the mixture to a mono-substituted imidazoline of the formula:

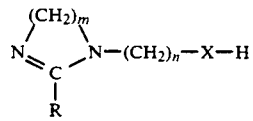

wherein R, m, n and X are as hereinbefore defined; the improvement comprising:

c) adding to said liquid reaction mixture formed in step (b), after drying if necessary to form an anhydrous mixture, both an esterifying agent and a catalytically effective amount of an esterification catalyst, said esterifying agent being selected from triglycerides of the formula:

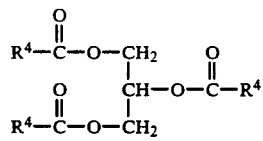

wherein the R$^4$s are, independently, C$_{11}$-C$_{21}$ hydrocarbyl groups;

said esterifying agent being present in an amount sufficient to provide a molar ratio of esterifying agent to acylating agent originally present in step (a) of from about 0.75:1 to 1.2:1;

said esterification catalyst being selected from Ti-(OR$^6$)$_4$, wherein R$^6$ is a C$_1$-C$_4$ alkyl group, TiY$_4$, wherein Y is a halide; SnT$_2$ wherein T is, independently, a C$_1$-C$_8$ hydrocarbyl group, a hydroxyl group, or a halide; and a dialkyltin chloride; and subsequently d) maintaining said anhydrous liquid reaction mixture at a temperature of from about 100° C. to 200° C. for a period of from about 1 hour to about 5 hours under an inert gas, producing a reaction product mixture containing one or more di-substituted imidazolines of the formula:

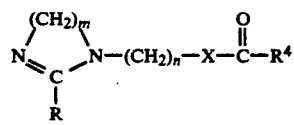

wherein R, R$^4$, m, n and X are as hereinbefore defined.

4. A solid fabric softening composition comprising from about 50% to 100% of the reaction mixture according to claim 1 wherein said composition being releasably affixed to a solid carrier.

* * * * *